US012657944B2

(12) United States Patent　　(10) Patent No.:　US 12,657,944 B2

Ullaskrishnan et al.　　(45) Date of Patent:　Jun. 16, 2026

---

(54) OCR-BASED EXTRACTION OF CLINICAL DATA FROM DICOM SC IMAGES

(71) Applicant: SIEMENS HEALTHINEERS AG, Forchheim (DE)

(72) Inventors: Poikavila Ullaskrishnan, Lebanon, NH (US); Ren-Yi Lo, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 485 days.

(21) Appl. No.: 18/298,400

(22) Filed: Apr. 11, 2023

(65) Prior Publication Data

US 2023/0343121 A1　　Oct. 26, 2023

(30) Foreign Application Priority Data

Apr. 22, 2022　(EP) .................................... 22169432

(51) Int. Cl.
　*G06V 30/148*　(2022.01)
　*G16H 30/40*　(2018.01)
　*G16H 50/70*　(2018.01)

(52) U.S. Cl.
　CPC ........... *G06V 30/153* (2022.01); *G16H 30/40* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 10,078,725 B2 | 9/2018 | Kalafut et al. | |
| 11,183,294 B2 | 11/2021 | Sargent et al. | |
| 2004/0252871 A1* | 12/2004 | Tecotzky | G16H 50/50 |
| | | | 382/128 |
| 2008/0109250 A1 | 5/2008 | Walker et al. | |
| 2013/0060579 A1 | 3/2013 | Yu et al. | |
| 2015/0254401 A1* | 9/2015 | Sankhe | G16H 30/40 |
| | | | 382/132 |
| 2021/0174503 A1* | 6/2021 | Trautwein | G16H 50/70 |

FOREIGN PATENT DOCUMENTS

| | | |
|---|---|---|
| CN | 103946885 A | 7/2014 |
| CN | 113972000 A | 1/2022 |
| CN | 114365181 A | 4/2022 |

OTHER PUBLICATIONS

Eapen et al., "DICODerma: A practical approach for metadata management of images in dermatology," Feb. 17, 2021, arXiv: 2102.08673v1, https://doi.org/10.48550/arXiv.2102.08673 (Year: 2021).*

(Continued)

*Primary Examiner* — Michelle M Koeth

(57) ABSTRACT

Techniques of facilitating processing of at least one DICOM SC image—e.g., using a PC or workstation in a hospital or an institution—to automatically extract clinical data therein are provided. Characters associated with the clinical data are extracted from the at least one DICOM SC image based on configuration information associated with the at least one DICOM SC image, which configuration information is obtained based on the at least one DICOM SC image.

17 Claims, 16 Drawing Sheets

(56) References Cited

OTHER PUBLICATIONS

Tsui et al., "Automatic Selective Removal of Embedded Patient Information From Image Content of DICOM Files," American Journal of Roentgenology 2012 198:4, 769-772. (Year: 2012).*

Graham et al., "DICOM demystified: A review of digital file formats and their use in radiological practice," Clinical Radiology (2005), 60 1133-1140, Elsevier Ltd., doi:10.1016/j.crad.2005.07.003. (Year: 2005).*

DICOM Tag Library. Retrieved Aug. 8, 2019. https://www.dicomlibrary.com/dicom/dicom-tags/ (Year: 2019).*

Crane et al., "SIVIC: Open-Source, Standards-Based Software for DICOM MR Spectroscopy Workflows," International Journal of Biomedical Imaging, vol. 2013, 2013, Article ID 169526, 12 pages, http://dx.doi.org/10.1155/2013/169526 (Year: 2013).*

Bridge et al., "Highdicom: A Python library for standardized encoding of image annotations and machine learning model outputs in pathology and radiology," Sep. 9, 2021, arXiv:2106.07806v2 [eess.IV], http://doi.org/10.48550/arXiv.2106.07806 (Year: 2021).*

Secondary Capture Image IOD. Retrieved Aug. 9, 2019. http://dicom.nema.org/medical/dicom/current/output/chtml/part03/sect_A.8.html (Year: 2019).*

Secondary Capture Image IOD. Retrieved Aug. 9, 2019. http://dicom.nema.org/medical/dicom/current/output/chtml/part03/sect_A.8.html.

P. M. Manwatkar and Kavita R. Singh, "A Technical Review on Text recognition from Images," 9th International Conference on Intelligent Systems and Control (ISCO), 2015, pp. 721-725.

DoseUtility Tool. Retrieved on Aug. 9, 2019. https://www.dclunie.com/pixelmed/software/webstart/DoseUtilityUsage.html.

Tsui, Gary and Chan, Tao, "Automatic Selective Removal of Embedded Patient Information from Image Content of DICOM Files". American Journal of Roentgenology 2012 198:4, 769-772.

Optical Character Recognition (OCR) Nicomsoft.com. Retrieved Aug. 8, 2019.

Tesseract Wiki. Retrieved Aug. 8, 2019. https://github.com/tesseract-ocr/tesseract/blob/master/doc/tesseract.1.asc https://tesseract.patagames.com/help/html/T_Patagames_Ocr_Enums_PageSegMode.htm.

DICOM Tag Library. Retrieved Aug. 8, 2019. https://www.dicomlibrary.com/dicom/dicom-tags/.

Gupta, Maya R.; Jacobson, Nathaniel P.; Garcia, Eric K. (2007). "OCR binarisation and image pre-processing for searching historical documents" (PDF). Pattern Recognition. 40 (2): 389. doi:10.1016/j.patcog.2006.04.043.

Methods to Improve OCR Quality. Retrieved Aug. 8, 2019. https://github.com/tesseract-ocr/tesseract/wiki/ImproveQuality.

Holley, Rose (Apr. 2009). "How Good Can It Get? Analysing and Improving OCR Accuracy in Large Scale Historic Newspaper Digitisation Programs". D-Lib Magazine.

Pydicom Library. Retrieved Aug. 8, 2019. https://pydicom.github.io/.

TIFF Image Format. Retrieved Aug. 8, 2019. https://www.loc.gov/preservation/digital/formats/fdd/fdd000072.shtml.

Extended European Search Report (EESR) mailed Sep. 22, 2022 in corresponding European Patent Application No. 22169432.6.

Kay, Anthony, "Tesseract: an Open-Source Optical Character Recognition Engine". Linux Journal. (Jul. 2007). Retrieved Sep. 28, 2011.

* cited by examiner

Threshold $=$ 130 HV
($90.5$ mg/cm$^3$ CaHA)

| Artery | Number of Lesions (1) | Volume [mm$^3$] (3) | Equiv. Mass [mg CaHA] (4) | Calcium Score (2) |
|---|---|---|---|---|
| LM | 0 | 0.0 | 0.00 | 0.0 |
| LAD | 3 | 229.4 | 53.60 | 293.7 |
| CX | 1 | 20.7 | 3.99 | 25.0 |
| RCA | 0 | 0.0 | 0.00 | 0.0 |
| Total | 4 | 250.0 | 57.57 | 318.7 |

| Area | | |
|---|---|---|
| Beat: 1/2 | | |
| FAC | 35.9 | % |
| Area min | 11.6 | cm² |
| Area max | 18.1 | cm² |

Longitudinal Strain   Endo

| Seg | PreStr | PkSys | PkAll | PSI | TPk Ovrl |
|---|---|---|---|---|---|
| | % | % | % | % | ms |
| 01-Lateral | | | -17.1 | | |
| 02-Lateral | | | -16.3 | | 541.0 |
| 03-Lateral Apex | | | -24.1 | | |
| 06-Septal Apex | 3.3 | | -14.8 | | 358.0 |
| 05-Septal | | | -13.7 | | -449.0 |
| 04-Septal | | | -12.4 | | 750.0 |
| Average | | | -16.41 | | |
| Standard Dev. | 0.00 | | 4.14 | | 1-00.99 |
| Global | | | -14.68 | | 8-97.00 |

Max Opp Wall Delay 419.0 ms (01-04)

401

402

RVS

REPORTINGDOCTOR 1

Figure 5:
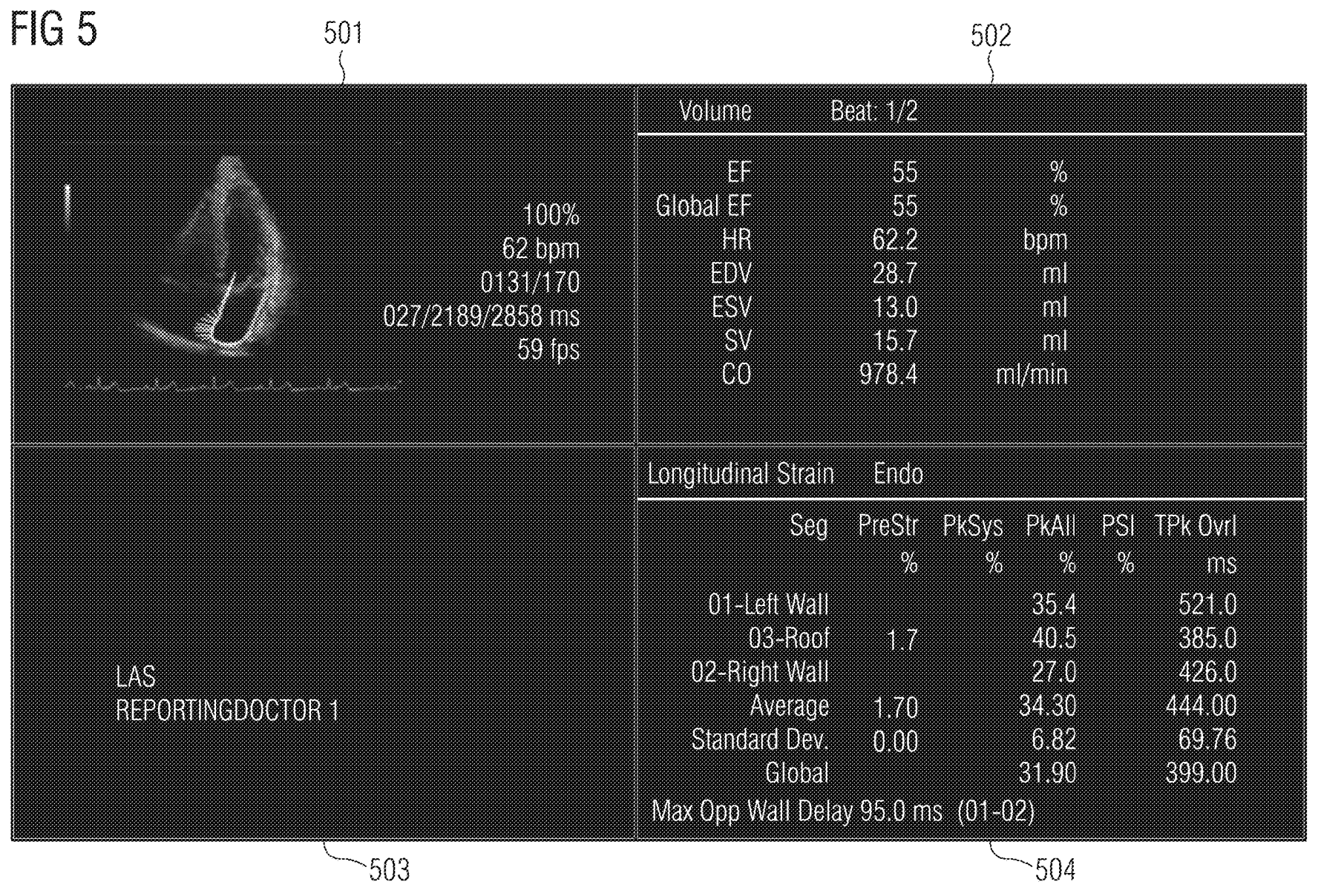

| Volume | Beat 1/2 | |
|---|---|---|
| EF | 55 | % |
| Global EF | 55 | % |
| HR | 62.2 | bpm |
| EDV | 28.7 | ml |
| ESV | 13.0 | ml |
| SV | 15.7 | ml |
| CO | 978.4 | ml/min |

504

| Longitudinal Strain Endo | | | | | |
|---|---|---|---|---|---|
| Seg | PreStr % | PkSys % | PkAll % | PSI % | TPk Ovrl ms |
| 01-Left Wall | 1.7 | | 35.4 | | 521.0 |
| 03-Roof | | | 40.5 | | 385.0 |
| 02-Right Wall | | | 27.0 | | 426.0 |
| Average | 1.70 | | 34.30 | | 444.00 |
| Standard Dev. | 0.00 | | 6.82 | | 69.76 |
| Global | | | 31.90 | | 399.00 |
| Max Opp Wall Delay 95.0 ms (01-02) | | | | | |

501

100%
62 bpm
0131/170
027/2189/2858 ms
59 fps

503

LAS
REPORTINGDOCTOR 1

2000 obtaining at least one DICOM SC image ~2010 obtaining configuration information associated with the at least one DICOM SC image based on the at least one DICOM SC image ~2020 extracting characters associated with clinical data from the at least one DICOM SC image based on the configuration information ~2030

| Volume | Beat: 1/2 | |
|---|---|---|
| EF | 55 | % |
| Global EF | 55 | % |
| HR | 62.2 | bpm |
| EDV | 28.7 | ml |
| ESV | 13.0 | ml |
| SV | 15.7 | ml |
| CO | 978.4 | ml/min |

| Longitudinal Strain | Endo | | | | |
|---|---|---|---|---|---|
| Seg | PreStr | PkSys | PkAll | PSI | TPkOvrl |
| | % | % | % | % | ms |
| 01-Left Wall | | | 35.4 | | 521.0 |
| 03-Roof | 1.7 | | 40.5 | | 385.0 |
| 02-Right Wall | | | 27.0 | | 426.00 |
| Average | 1.70 | | 34.30 | | 444.00 |
| Standard Dev. | 0.00 | | 6.82 | | 69.76 |
| Global | | | 31.90 | | 399.00 |
| Max Opp Wall Delay 95.0 ms  (01-02) | | | | | |

100%
62 bpm
0131/170
027/2189/2858 ms
59 fps

LAS
REPORTINGDOCTOR 1

501
502
503
504

| Volume | Beat 1/2 | |
|---|---|---|
| EF | 55 | % |
| Global EF | 55 | % |
| HR | 62.2 | bpm |
| EDV | 28.7 | ml |
| ESV | 13.0 | ml |
| SV | 15.7 | ml |
| CO | 978.4 | ml/min |

| Longitudinal Strain | Endo | | | | |
|---|---|---|---|---|---|
| Seg | PreStr | PkSys | PkAll | PSI | TPk Ovrl |
| | % | % | % | % | ms |
| 01-Left Wall | | | 35.4 | | 521.0 |
| 03-Roof | 1.7 | | 40.5 | | 385.0 |
| 02-Right Wall | | | 27.0 | | 426.0 |
| Average | 1.70 | | 34.30 | | 444.00 |
| Standard Dev | 0.00 | | 6.82 | | 69.76 |
| Global | | | 31.90 | | 399.00 |
| Max Opp Wall Delay 95.0 ms (01-02) | | | | | |

100%
62 bpm
0131/170
027/2189/2858 ms
59 fps

LAS
REPORTINGDOCTOR 1 splitting

| Volume Beat: 1/2 | | |
|---|---|---|
| EF | 55 | % |
| Global EF | 55 | % |
| HR | 62.2 | bpm |
| EDV | 28.7 | ml |
| ESV | 13.0 | ml |
| SV | 15.7 | ml |
| CO | 978.4 | ml/min |

2040 → splitting

| Volume Beat: 1/2 | | |
|---|---|---|
| EF | 55 | % |
| Global EF | 55 | % |
| HR | 62.2 | bpm |
| EDV | 28.7 | ml |
| ESV | 13.0 | ml |
| SV | 15.7 | ml |
| CO | 978.4 | ml/min |

2050 → OCR

| Volume | Beat: 1/2 |
|---|---|
| EF | 55 |
| Global EF | 55 |
| HR | 62.2 |
| EDV | 28.7 |
| ESV | 13 |
| SV | 15.7 |
| CO | 978.4 |

2060 →

| EDV | 28.7 |
|---|---|
| ESV | 13 |
| SV | 15.7 |

Longitudinal Strain    Endo

| Seg | PreStr | PkSys | PkAll | PSI | TPk Ovrl |
|---|---|---|---|---|---|
| | % | % | % | % | ms |
| 01-Left Wall | | | 35.4 | | 521.0 |
| 03-Roof | 1.7 | | 40.5 | | 385.0 |
| 02-Right Wall | | | 27.0 | | 426.0 |
| Average | 1.70 | | 34.30 | | 444.00 |
| Standard Dev | 0.00 | | 6.82 | | 69.76 |
| Global | | | 31.90 | | 399.00 |

Max Opp Wall Delay 95.0 ms (01-02)

3010 → splitting

Longitudinal Strain    Endo

| Seg | PreStr | PkSys | PkAll | PSI | TPk Ovrl |
|---|---|---|---|---|---|
| | % | % | % | % | ms |
| 01-Left Wall | | | 35.4 | | 521.0 |
| 03-Roof | 1.7 | | 40.5 | | 385.0 |
| 02-Right Wall | | | 27.0 | | 426.0 |
| Average | 1.70 | | 34.30 | | 444.00 |
| Standard Dev | 0.00 | | 6.82 | | 69.76 |
| Global | | | 31.90 | | 399.00 |

Max Opp Wall Delay 95.0 ms (01-02)

3020 → splitting

Longitudinal Strain    Endo

| Seg | PreStr | PkSys | PkAll | PSI | TPk Ovrl |
|---|---|---|---|---|---|
| | % | % | % | % | ms |
| 01-Left Wall | | | 35.4 | | 521.0 |
| 03-Roof | 1.7 | | 40.5 | | 385.0 |
| 02-Right Wall | | | 27.0 | | 426.0 |
| Average | 1.70 | | 34.30 | | 444.00 |
| Standard Dev | 0.00 | | 6.82 | | 69.76 |
| Global | | | 31.90 | | 399.00 |

Max Opp Wall Delay 95.0 ms (01-02)

FIG 11B

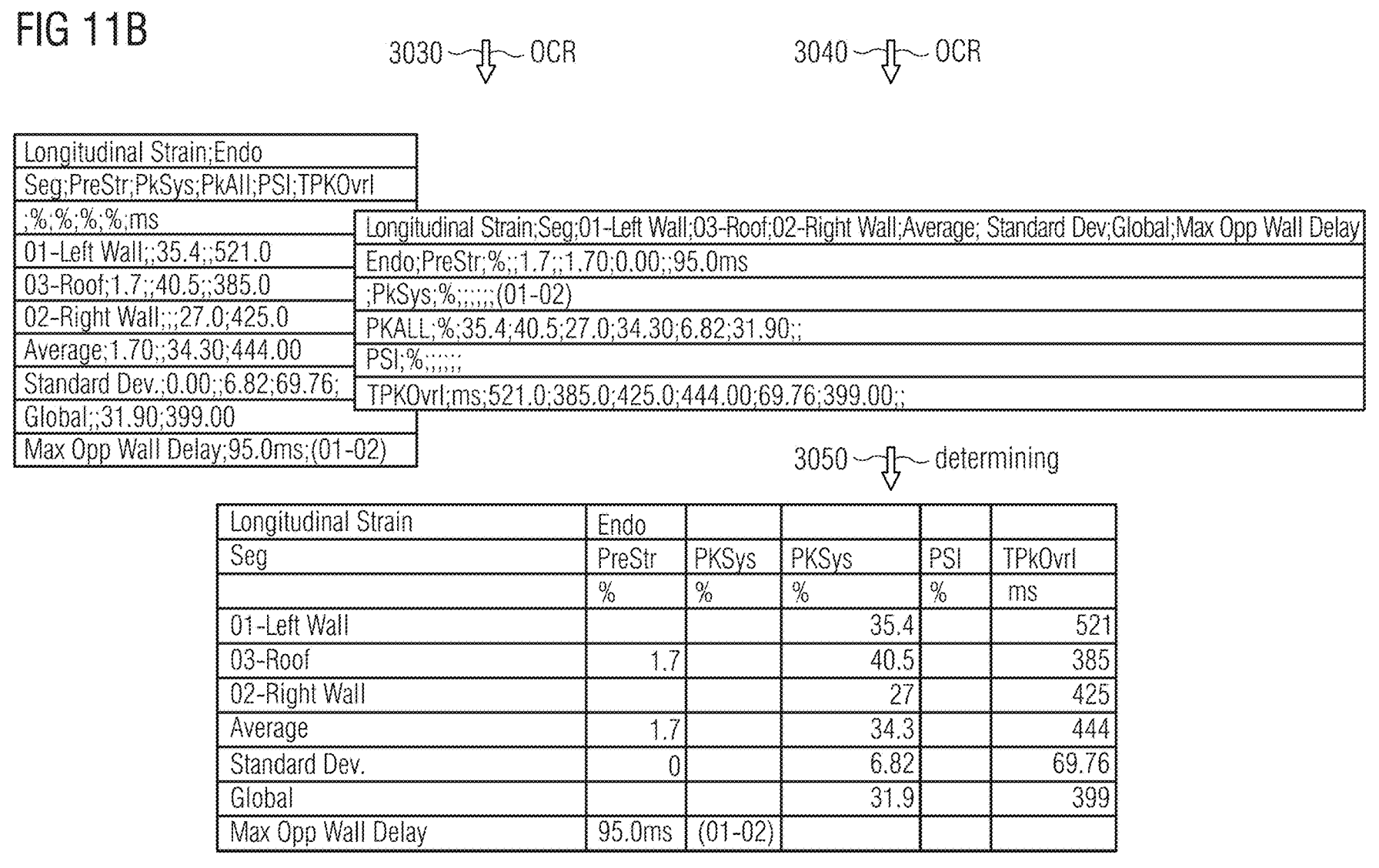

3030 → OCR

3040 → OCR

3050 → determining

```
Longitudinal Strain:Endo
Seg;PreStr;PkSys;PkAll;PSI;TPKOvrl
;%;%;%;%;ms
01-Left Wall;;35.4;;;521.0
03-Roof;1.7;;40.5;;385.0
02-Right Wall;;;27.0;425.0
Average;1.70;;34.30;444.00
Standard Dev.;0.00;;6.82;69.76;
Global;31.90;399.00
Max Opp Wall Delay;95.0ms;(01-02)
```

```
Longitudinal Strain:Seg;01-Left Wall;03-Roof;02-Right Wall;Average; Standard Dev;Global;Max Opp Wall Delay
Endo;PreStr;%;;1.7;;1.70;0.00;;95.0ms
;PkSys;%;;;;(01-02)
PKALL;%;35.4;40.5;27.0;34.30;6.82;31.90;
PSI;%;;;;;
TPKOvrl;ms;521.0;385.0;425.0;444.00;69.76;399.00;;
```

| Longitudinal Strain | Endo | | | | |
|---|---|---|---|---|---|
| Seg | PreStr | PkSys | PkSys | PSI | TPKOvrl |
| | % | % | % | % | ms |
| 01-Left Wall | | | 35.4 | | 521 |
| 03-Roof | 1.7 | | 40.5 | | 385 |
| 02-Right Wall | | | 27 | | 425 |
| Average | 1.7 | | 34.3 | | 444 |
| Standard Dev. | 0 | | 6.82 | | 69.76 |
| Global | | | 31.9 | | 399 |
| Max Opp Wall Delay | 95.0ms | (01-02) | | | |

| PatientID | StudyID | AccessionNumber | StudyDate | EDV(ml) | ESV (ml) | SV(ml) | 01-LeftWall_PreStr | Average_PreStr | 01-LeftWall-PkAll | Average_PkAll | Global-PkAll |
|---|---|---|---|---|---|---|---|---|---|---|---|
| PatID1 | 123456 | 8888888 | 20190101 | 28.7 | 13 | 15.7 | N/A | 1.7 | 35.4 | 34.3 | 31.9 |

OCR-BASED EXTRACTION OF CLINICAL DATA FROM DICOM SC IMAGES

RELATED APPLICATION

This application claims the benefit of EP 22169432.6, filed Apr. 22, 2022, which is hereby incorporated by reference in its entirety

TECHNICAL FIELD

Various examples of the disclosure relate to facilitating processing of Digital Imaging and Communications in Medicine (DICOM) Secondary Capture (SC) images to automatically extract relevant clinical data therein. Various examples of the disclosure specifically relate to extracting characters associated with clinical data from at least one DICOM SC image based on configuration information associated with the at least one DICOM SC image, which is obtained based on the at least one DICOM SC image.

BACKGROUND

DICOM is one of the most popular file formats for storing, transmitting, and viewing medical images. The SC Image Information Object Definition (IOD) specifies images that are converted from a non-DICOM format to a modality independent DICOM format. I.e., a DICOM SC image could be regarded as an image that is converted from a non-DICOM format to a modality independent DICOM format. DICOM SC images can hold important curated clinical data that allow a better understanding of the accompanying DICOM images of a study of a patient, giving the physicians additional clinical context of the patient. For example, this could be strain information, calcium scores, or cardiovascular volumes. DICOM SC images are created, for example, by image post-processing tools in the scanner or by screen captures of the scanner display, such as an ultrasound scanner display. They are manually viewed along with the other DICOM images during diagnosis stages by the radiologists and then discarded. The data in them could be useful for future research as the data provides more contextual information to the DICOM header tags and other scan images in the acquisition.

SC images have a heterogeneous format and the relevant data in the SC images vary depending on the use case. Hence, there is no constant definition of what is needed and what is not. Further, SC images have a heterogeneous structure and the content pattern of SC images varies widely based on the source software version, the scanner, and the configuration of the installation.

There is thus no one-size-fits-all solution for extracting clinical data from various SC images since not every data is relevant from SC images and not every SC image is equal in design. The major reason that they are not used in research, despite their value, is the enormous labor cost and time needed to extract the data that is burnt into the pixel image. Despite advances in Image-to-text research, such as techniques discloses in a non-patent literature—Manwatkar, Pratik Madhukar, and Shashank H. Yadav. "Text recognition from images." 2015 *International Conference on Innovations in Information, Embedded and Communication Systems (ICIIECS)*. IEEE, 2015, a viable solution has never been developed that allows the user to extract what is needed from whatever type of SC image.

Due to the popular domain of image-text and Optical Character Recognition (OCR) research, e.g., "Optical Character Recognition (OCR)—How it works"—described in Nicomsoft.com, there have been efforts to use OCR within the DICOM image domain. Due to the varied content in SC images, the relevant data differs based on the use case. Hence, there have been efforts to extract particular information from particular types of SC images. These tools are purpose-built for the sole purpose of extracting a specific variable for the use case. An example is DoseUtility, which uses OCR to extract radiant dose information from General Electric (GE), Siemens, or Toshiba Computed Tomography (CT) SC images. These images have particular series codes based on the manufacturer and thus have a well-defined pattern. DoseUtility thus works very well to extract the dose information from these SC images since the required variable is well-defined and the pattern as well. The disadvantage is of course that it is purpose-built and cannot be used to extract any other information from the same SC image or the same information from a non-standardized SC image. This is also the major drawback of such tools. There are many such dedicated software programs available, but they only serve a specific purpose and cannot be used in other use cases.

A further exemplary OCR-based technique is directed to removing Patient Health Information (PHI). Reliable PHI removal is an important aspect of medical research as removal allows data sharing while complying with the local data privacy laws. Since SC images are sometimes screen captures of scanners, they usually contain the patient data embedded into the SC images. Hence, there have been efforts to use OCR to identify and remove PHI from SC images, such as techniques disclosed by Tsui, Gary Kin-wai, and Tao Chan, in "Automatic selective removal of embedded patient information from image content of DICOM files." *American Journal of Roentgenology* 198.4 (2012): 769-772. Such literature uses the open-source Tesseract OCR to extract characters from SC images and then looks for words that match with the PHI in the DICOM header tags. For example, the approach checks if the PatientName tag value in the DICOM header is present in the extracted characters. The advantage, as opposed to DoseUtility, is that this approach works on any kind of SC image. But since the approach is purpose-built to remove PHI, the program only identifies words that match the value of specific PHI DICOM tags. The approach cannot be used by the user to extract relevant clinical information from SC images. Thus, similar to DoseUtility, these efforts serve a specific purpose and cannot be used within a research context to extract values of specific user-defined variables.

Consequently, the existing techniques cannot allow the user to define what he or she needs and cannot also work on arbitrarily user-selected SC images. That is, there is no versatile technique that can be used to extract whatever clinical data a user needs for any kind of SC image.

SUMMARY

Accordingly, there is a need for advanced techniques that mitigate or overcome the above-identified drawbacks or restrictions. There is a need for advanced techniques of automatically extracting whatever clinical data a user needs for any kind of SC image.

Hereinafter, techniques of facilitating processing of at least one DICOM SC image—e.g., using a PC or workstation in a hospital or an institution—to automatically extract clinical data therein will be described. Characters associated with the clinical data are extracted from the at least one DICOM SC image based on configuration information associated with the at least one DICOM SC image, which is obtained based on the at least one DICOM SC image.

A computer-implemented method is provided. The method is used to process at least one DICOM SC image to automatically extract clinical data therein. The method includes obtaining at least one DICOM SC image and obtaining configuration information associated with the at least one DICOM SC image based on the at least one DICOM SC image. The method further includes extracting characters associated with clinical data from the at least one DICOM SC image based on the configuration information.

A computer program or a computer-program product or a non-transitory computer-readable storage medium that includes program code is provided. The program code can be loaded and executed by at least one processor. Upon loading and executing the program code, the at least one processor processes at least one DICOM SC image to automatically extract clinical data therein. At least one DICOM SC image is obtained, and configuration information associated with the at least one DICOM SC image is obtained based on the at least one DICOM SC image. Further, characters associated with clinical data are extracted from the at least one DICOM SC image based on the configuration information.

A computing device including at least one processor and at least one memory is provided. The at least one processor is configured to load program code from the at least one memory and execute the program code. Upon executing the program code, the at least one processor is configured to process at least one DICOM SC image to automatically extract clinical data therein. The at least one processor is configured to obtain at least one DICOM SC image, and obtain configuration information associated with the at least one DICOM SC image based on the at least one DICOM SC image. The at least one processor is further configured to extract characters associated with clinical data from the at least one DICOM SC image based on the configuration information.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 2 schematically illustrates another exemplary DICOM SC image.

FIG. 5 schematically illustrates a still further exemplary DICOM SC image.

FIG. 10 schematically illustrates an exemplary workflow for extracting row-wise characters.

FIG. 11 (FIGS. 11A and 11B) schematically illustrates an exemplary workflow for extracting tabular characters.

DETAILED DESCRIPTION OF THE DRAWINGS

Figure 1:
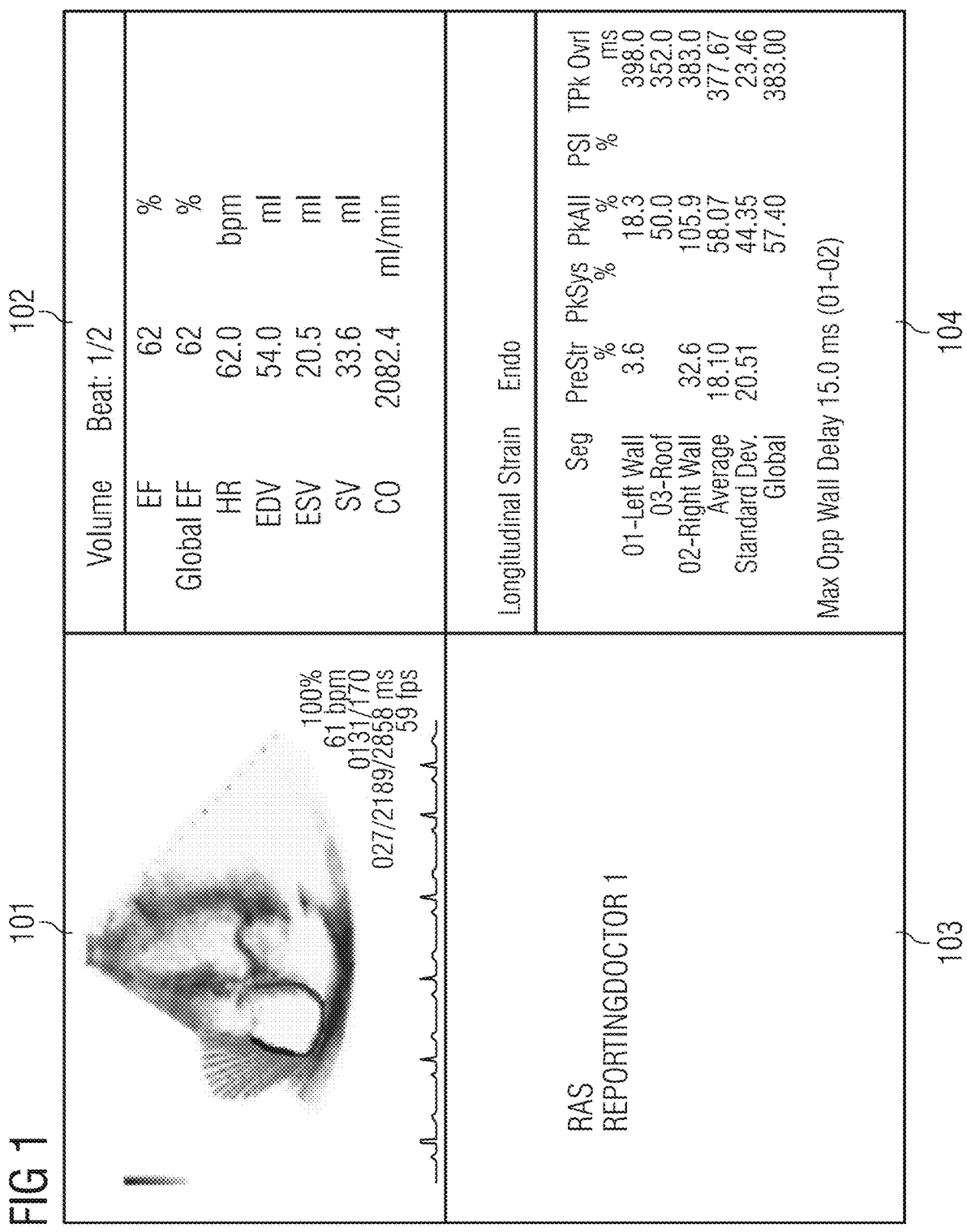
FIG. 1 schematically illustrates an exemplary DICOM SC image.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques disclosed herein generally relate to facilitating processing of at least one DICOM SC image— e.g., using a PC or workstation in a hospital or an institution—to automatically extract clinical data therein. Characters associated with the clinical data are extracted from the at least one DICOM SC image based on configuration information associated with the at least one DICOM SC image, which is obtained based on the at least one DICOM SC image.

The at least one DICOM SC image may be obtained from a data repository, e.g., a Picture Archiving and Communication System (PACS). Alternatively, or additionally, the at least one DICOM SC image may be directly obtained from a medical imaging scanner, such as an X-ray radiography scanner, an ultrasound scanner, a computed tomography (CT) scanner, a positron emission tomography (PET) scanner, or a magnetic resonance imaging (MRI) scanner. Therefore, the at least one DICOM SC image may be associated with one or more medical images, for example, X-ray radiography images, ultrasound images, CT images, PET images, or MRI images. For example, the at least one DICOM SC image may be created by image post-processing tools/software running in any one of an X-ray scanner, CT scanner, PET scanner, or MRI scanner, or by screen captures of a display connected/connectable to any one of an X-ray scanner, CT scanner, PET scanner, or MRI scanner. Four exemplary DICOM SC images are illustrated in FIGS. 1-4, respectively. In this disclosure, the terminology "DICOM SC image(s)" is equivalent to "SC image(s)". The exemplary DICOM SC images illustrated in FIGS. 1-4 are used for illustrative purposes, which may not look the same as clinical DICOM SC images.

Figure 3:
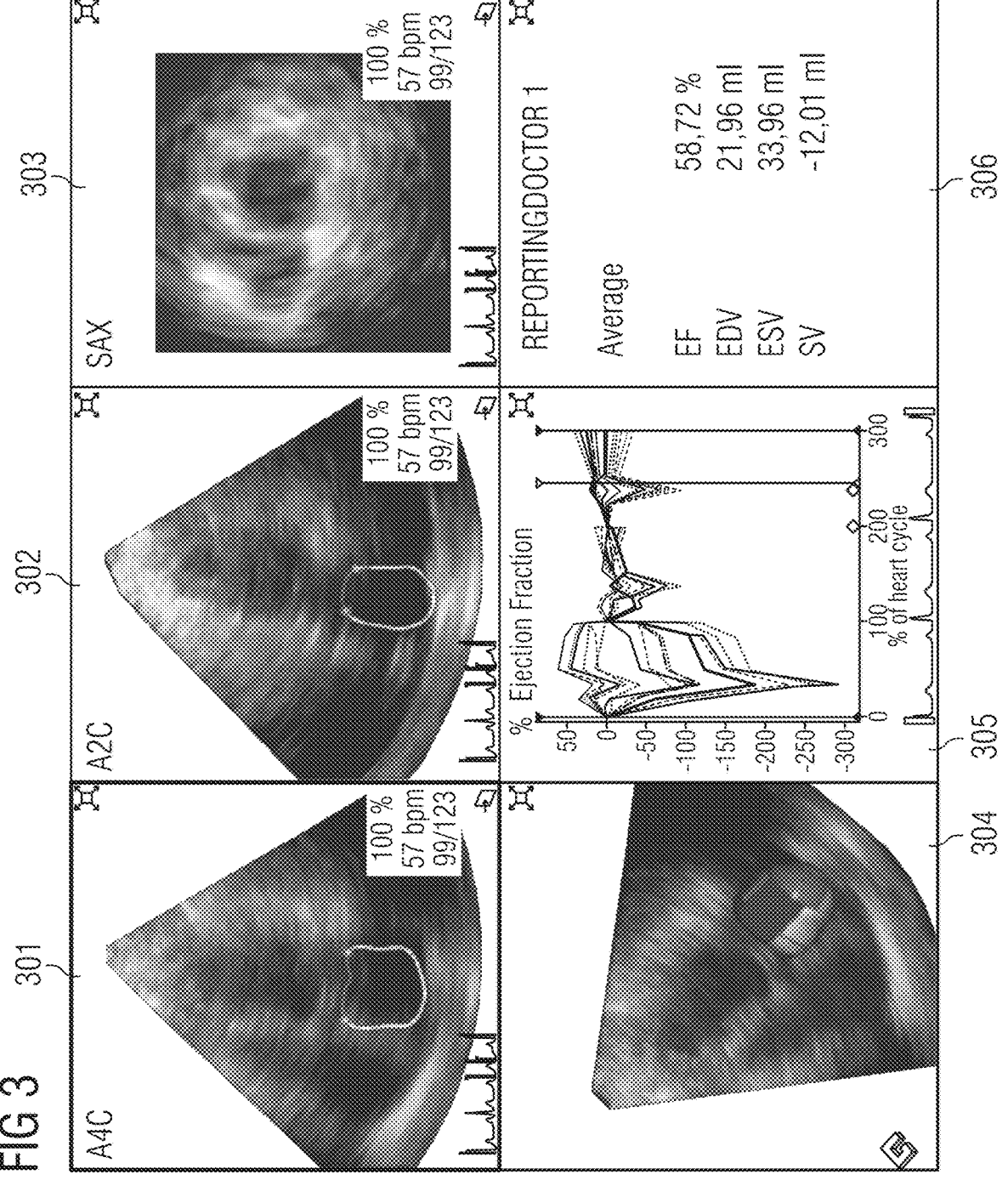
FIG. 3 schematically illustrates a further exemplary DICOM SC image.
Figure 4:
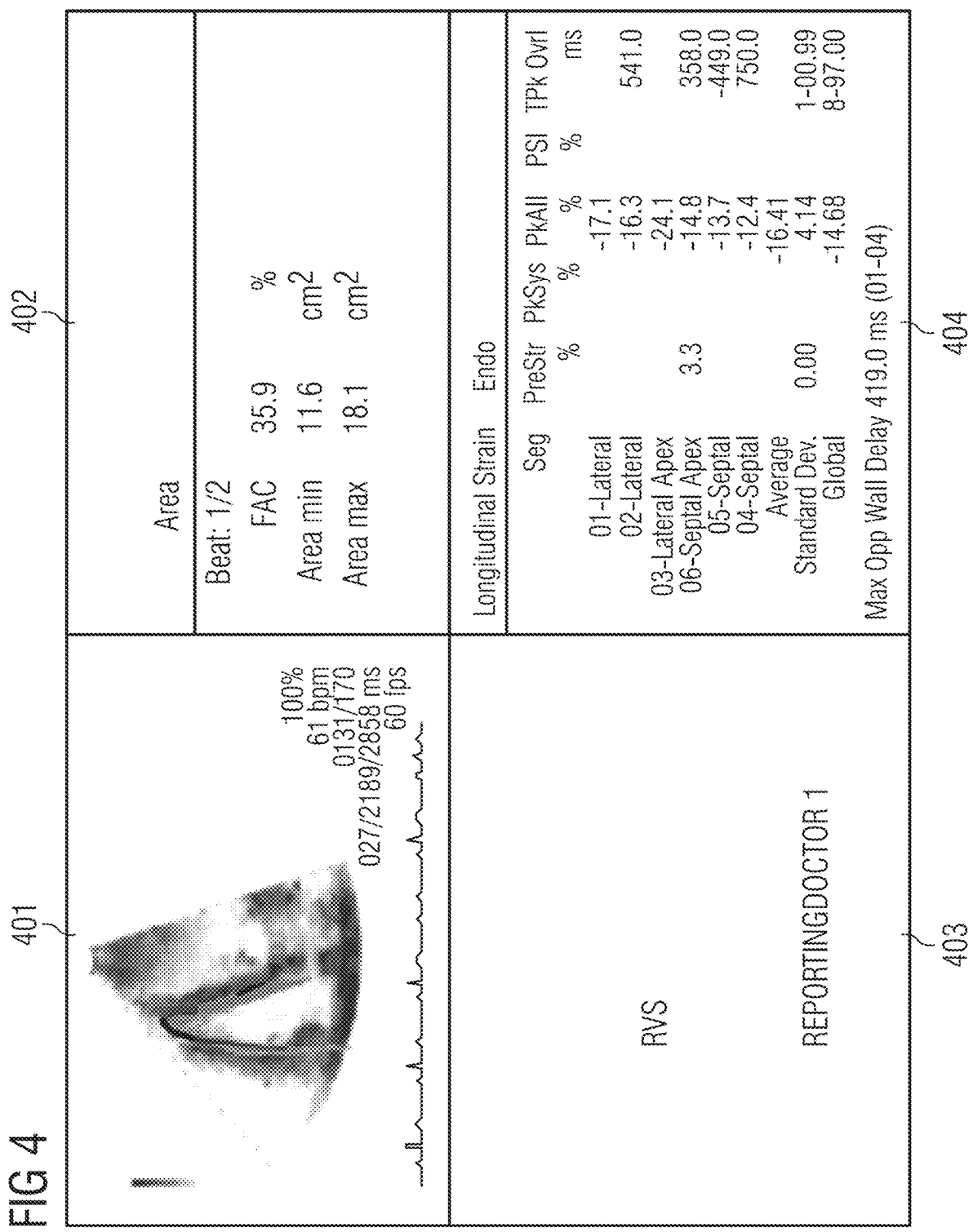
FIG. 4 schematically illustrates a still further exemplary DICOM SC image.

FIG. 1 depicts an exemplary DICOM SC image with a 2*2 grid-size. I.e., the exemplary DICOM SC image shown in FIG. 1 has four sections (quadrants) 101, 102, 103, and 104, among which there are two sections, i.e., 102 and 104, containing characters associated with clinical data. Similarly, FIG. 2 depicts another exemplary DICOM SC image with a 1*1 grid-size, i.e., only one section 201 which contains characters associated with clinical data. FIG. 3 depicts a further exemplary DICOM SC image with a 2*3 grid-size, i.e., six sections 301-306, among which only section 306 contains characters associated with clinical data. FIG. 4 depicts a still further exemplary DICOM SC image with a 2*2 grid-size, i.e., four sections 401-404, among which quadrats 402 and 404 respectively contain characters associated with clinical data. Each of the four exemplary DICOM SC images may respectively represent a specific type of DICOM SC image.

According to the disclosure, the at least one DICOM SC image may contain characters associated with clinical data associated with an anatomical target region of a patient, e.g., the heart, the liver, the brain, or a part thereof.

In general, an SC image can include multiple characters associated with clinical data but not every character is needed, e.g., for a further use. The specific data that are needed to be extracted from the SC image may be defined by the configuration information associated with the at least one DICOM SC image. For example, the configuration may include one or more keywords of the characters associated with the clinical data, e.g., volume and/or longitudinal strain as shown in FIG. 5. Alternatively, or additionally, the configuration may include one or more pre-defined variables associated with the clinical data including, for example, one or more row names, and/or one or more column names. For example, referring to FIG. 5, such row names may be EF, Global EF, HR, EDV, ESV, SV, CO in section 502, as well as 01-Left Wall, 03-Roof, 02-Right Wall, Average, Standard Dev, Global in section 504. Column names may be Seg, PreStr, PKSys, PkAll, PSI, TPk Ovrl in section 504. The more specific the keywords and/or the pre-defined variables are, the more accurate the results of the extracted characters would be. Hence, the configuration information may also include information about sections in an SC image and/or an orientation of a table in the SC image.

For example, the configuration information associated with the SC image depicted in FIG. 5 may include a keyword—Volume, and/or pre-defined variables—EDV, ESV, and SV. According to such configuration information, which section(s) containing the characters to be extracted can be determined by the keyword—Volume, i.e., section 502, and/or which rows the characters to be extracted are located can be determined by the pre-defined variables—EDV, ESV, and SV, i.e., the three rows starting with EDV, ESV, and SV, respectively. If the configuration information only includes one or more keywords, all the characters in section(s) which contain(s) the one or more keywords may be extracted. Similarly, if the configuration information only includes one or more pre-defined variables, all the characters in the same row(s) or the same column(s) as the one or more pre-defined variables may be extracted. Alternatively, the configuration information associated with the SC image depicted in FIG. 5 may include a keyword—longitudinal strain, and a combination of pre-defined variables—(Average, PkAll). Then, section 504 is determined as the section containing the characters to be extracted, and character(s) being positioned in the same row as Average and the same column as PkAll is the character(s) to be extracted, i.e., 34.30 as shown in FIG. 5.

Alternatively, or additionally, the configuration may include a grid-size of each of the at least one DICOM SC image, e.g., 2*2 of the SC image shown in FIG. 5, and/or 2*3 of the SC image shown in FIG. 3. The accuracy of extracting the characters associated with clinical data may be improved by splitting the whole SC image into sub-images according to the grid-size.

Figure 6:
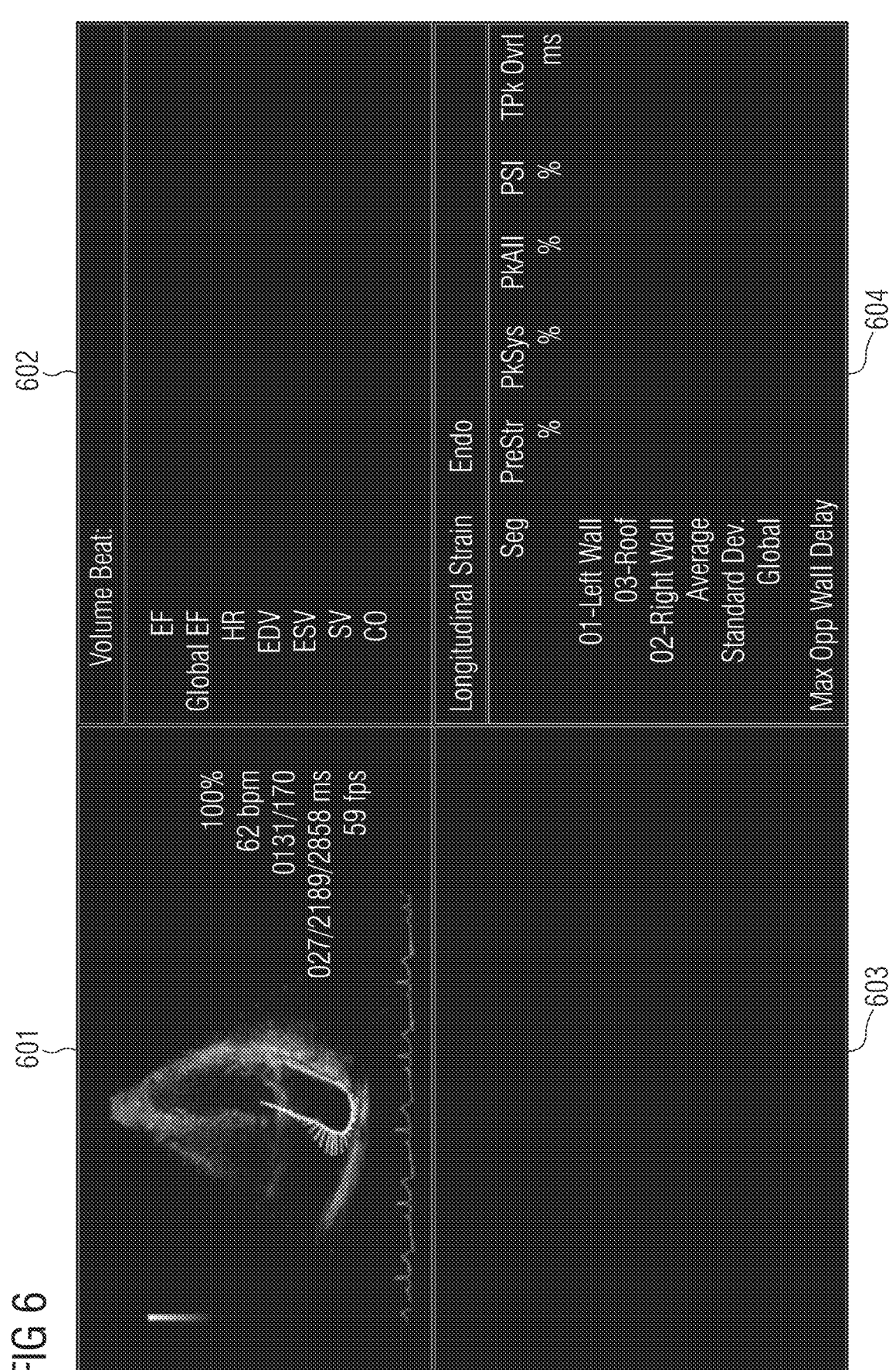
FIG. 6 schematically illustrates an exemplary template corresponding to the exemplary DICOM SC image of FIG. 5.

Alternatively, or additionally, the configuration information may include a template of the at least one DICOM SC image. Such a template may include all the common information shared by the same type of DICOM SC images. Herein, the same type of SC images may be SC images sharing the same grid-size, the same row names, and/or the same column names. For example, an exemplary template corresponding to the SC image shown in FIG. 5 is illustrated in FIG. 6. Such an exemplary template has a 2*2 grid-size, i.e., four sections 601-602, and the same row and column names as those of the SC image shown in FIG. 5, i.e., sections 602 and 604, respectively. Additionally, or optionally, the medical image within section 601 may be removed or replaced with an indication which indicates that section 601 contains a medical image but not characters associated with clinical data. Based on such a template, it is possible to accurately split SC images into sub-images or sections.

Optionally or additionally, the configuration information may include an output format of the extracted characters associated with clinical data, such as an Excel file or a json (JavaScript Object Notation) file. Optionally, or additionally, a required structure of content may be also defined in connection with the output format. For example, the output format may be in Excel format with one row per SC image, and the column names of the Excel format may include one or more pre-defined variables contained in the configuration information. Such an output format can facilitate utilization of the extracted characters, e.g., for diagnosis or research. For example, the extracted characters and corresponding DICOM images may be used for deep-learning and/or data-mining research. Additionally, or optionally, the extracted characters may be added into DICOM tags of the series containing the SC image. The extracted characters in conjunction with data available in other DICOM tags and other scan images help in improving research by providing more contextual information. The extracted characters also help in cohort selections of patients and classifying datasets based on the variable values in SC images.

According to various examples, the configuration information associated with the at least one DICOM SC image may be obtained by user inputs based on the at least one SC image. For example, the user may input the configuration information to a computing device, e.g., a PC or workstation, which is used to process SC images based on what is needed to be extracted, e.g., by defining one or more keywords and/or one or more pre-defined variables. Alternatively, or additionally, the configuration information may be automatically determined based on specific structure and/or content pattern of SC images to be processed, which are determined by, e.g., using image analysis techniques. Such image analysis techniques may include at least one of object recognition, image segmentation. Additionally, or optionally, the configuration information may be automatically determined based on IOD of the at least one DICOM SC image, such as IOD modules associated with patient, study, series, equipment, image as specified according to DICOM standards.

According to this disclosure, OCR may be used to extract one or more characters associated with clinical data from at least one DICOM SC image based on the configuration information explained above. OCR is the electronic or mechanical conversion of images of typed, handwritten or printed text into machine-encoded text, whether from a scanned document, a photo of a document, a scene-photo (for example, the text on signs and billboards in a landscape photo) or from subtitle text superimposed on an image (for example, from a television broadcast). Various OCR software is available and may be applied to this disclosure, such as, Tesseract Open Source OCR as presented in non-patent literature—Kay, Anthony. "Tesseract: an open-source optical character recognition engine." *Linux Journal* 2007.159 (2007): 2, GOCR (or JOCR), Cognitive OpenOCR (i.e., CuneiForm), Kraken, and A9T9. This disclosure will be explained in connection with Tesseract as an example.

According to various examples, when utilizing Tesseract OCR, a parameter of Tesseract OCR—page segmentation mode (PSM)—may be used to improve the accuracy of OCR results. The PSM explains the layout of the data and the form of the image to be processed. More information on PSM can be found on the Tesseract OCR Wiki page, e.g., https://github.com/tesseract-ocr/tesseract/blob/master/doc/tesseract.1.asc. Different PSMs may be suitable for different arrangements of the characters, e.g., row-wise, column-wise, or tabular. For example, PSM 7 assumes that each image is a single text/character line, and PSM 4 assumes that each image is a single column of text/character of variable sizes. I.e., PSMs 4 and 7 are respectively suitable for processing column-wise and row-wise characters.

As outlined above, by obtaining configuration information associated with at least one DICOM SC image, and further extracting characters associated with clinical data from the at least one DICOM SC image based on the obtained configuration information, characters associated with whatever clinical data can be automatically extracted for any kind of SC image. The configuration information may rely on a specific type of the at least one SC image and thereby the extraction of characters may be adapted to such a specific type based on the configuration information. Accordingly, the accuracy and efficiency of the extraction of the characters can be improved.

Figure 7:
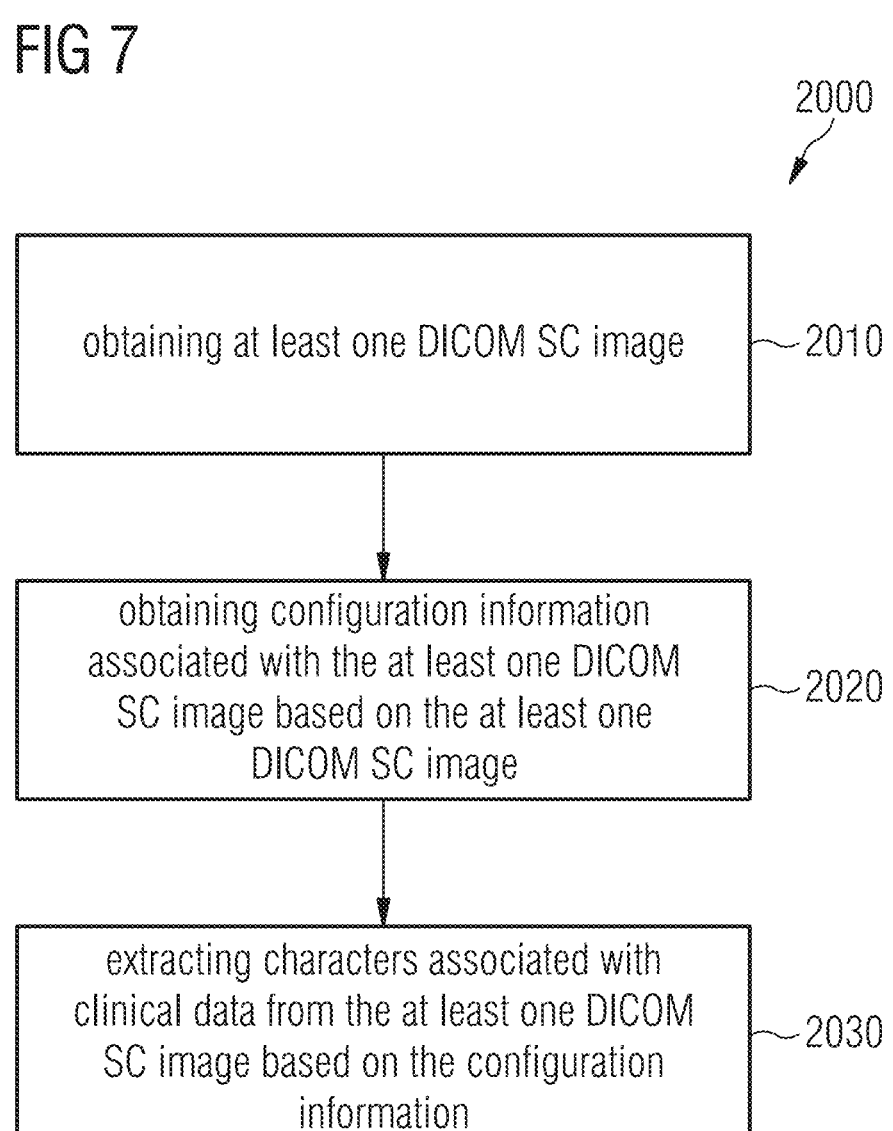
FIG. 7 is a flowchart of a method according to various examples.

FIG. 7 is a flowchart of a computer-implemented method 2000 according to various examples. The method 2000 pertains to processing at least one DICOM SC image to extract clinical data therein. Characters associated with the clinical data are extracted from the at least one DICOM SC image based on configuration information associated with the at least one DICOM SC image, which configuration information is obtained based on the at least one DICOM SC image.

The method 2000 may be executed by a computer or a workstation including at least one processing unit (processor) upon loading program code. The computer or the workstation may be positioned in a local network of a hospital or an institution. The computer or the workstation may be connected/connectable to a PACS, or directly to a medical imaging scanner. Alternatively, the computer or the workstation may be a node (server) of a cloud-based computing system or of an edge computing system. Details of the method 2000 are described below.

At block 2010, at least one DICOM SC image is obtained. The at least one DICOM SC image could be loaded from a PACS. Block 2010 could include controlling a medical imaging scanner, such as an MRI scanner to acquire DICOM images and to generate the at least one SC image by post-processing tools/software running in the medical imaging scanner. Alternatively, the at least one DICOM SC image may be received directly from a medical imaging scanner during a scan to perform a real-time examination of a patient.

At block 2020, configuration information associated with the at least one DICOM SC image are obtained based on the at least one DICOM SC image.

The configuration information associated with the at least one DICOM SC image may be obtained by user inputs based on the at least one SC image. Alternatively, or additionally, the configuration information may be obtained based on specific structure and/or content pattern of the at least one SC image. Alternatively, or additionally, the configuration information may be obtained based on DICOM tags of the at least one DICOM SC image.

At block 2030, characters associated with clinical data are extracted from the at least one DICOM SC image based on the configuration information.

The characters associated with the clinical data may be extracted using OCR. The configuration information may associate with a specific type of the at least one SC image and thereby the extraction of characters may be adapted to such a specific type based on the configuration information. Accordingly, the accuracy and efficiency of the extraction of the characters can be improved.

OCR can be applied on the whole SC image, but its accuracy cannot be sufficient. Noise and sparsity are exemplary factors that can drastically deteriorate the performance of any OCR algorithm as explained by Gupta, Maya R., Nathaniel P. Jacobson, and Eric K. Garcia in "OCR binarizaton and image pre-processing for searching historical documents." *Pattern Recognition* 40.2 (2007): 389-397. Since the data that needs to be extracted forms only one part of an image, it is best to condense pixel data of the at least one DICOM SC image to only those regions that need OCR extraction. Accordingly, the method 2000 may optionally include the following pre-processing acts.

The at least one DICOM SC image may be converted to any one of the following image formats: tag image file format, TIFF, raw image format, RAW, bitmap image file format, BMP, and portable network graphic format, PNG. Detailed explanation will be described in connection with TIFF in the following.

In this act, the pixel data of the secondary capture DICOM may be extracted and stored separately as a raw image format. TIFF format could be used since it handles lossless compression, can be used across multiple devices and operating systems, and requires less storage space than RAW image format as described in international standard—ISO 12639:2004. Graphic technology—Prepress digital data exchange—Tag image file format for image technology (TIFF/IT). Lossless compression may be required to maintain the image quality and thus also improve the OCR accuracy. Storage size would be also a major requirement since many DICOM SC images may be processed at once and hence should not take up a lot of temporary storage size. The TIFF files being generated may be temporary files for the purpose of OCR extraction and may be deleted once the output of the extraction is created.

Further, margins of the at least one DICOM SC image may be trimmed. Alternatively, or additionally, margins of the converted TIFF images of the at least one DICOM SC image may be trimmed. Optionally, automated margin alignment may be applied to the at least one DICOM SC image and/or the converted TIFF images of the at least one DICOM SC image.

After trimming margins, characters to be extracted may be large enough to achieve a high accuracy for some SC images, e.g., the SC image shown in FIG. 2, in which the SC image only contains one section, i.e., 1*1 grid-size. In such a case, splitting may not be needed but only trimming the margins would be enough so that the content can be as focused as possible. However, for some other SC images, e.g., those shown in FIGS. 1, 3, 5, and 5, the accuracy of extraction of characters may be further improved by splitting the SC image to sub-images. I.e., the at least one DICOM SC image or the converted TIFF images of the at least one DICOM SC image may be split to sub-images to concentrate the OCR only on those regions that contain the characters to be extracted. To decide where these sub-images are would be very much dependent on the content of the SC image and on the characters to be extracted.

Accordingly, the method 2000 may optionally further include splitting the at least one DICOM SC image into sub-images based on the configuration information, and selecting one or more sub-images containing the characters associated with the clinical data from the split sub-images, wherein extracting the characters includes respectively extracting the characters from the selected one or more sub-images. If the at least one SC image is converted to TIFF image, the same splitting and selecting process could be applied to the converted TIFF images of the at least one DICOM SC image.

The configuration information may include a grid-size of the at least one DICOM SC image and/or one or more keywords of the characters associated with the clinical data, and the splitting may be based on the grid-size and/or the one or more keywords. The one or more keywords may be determined by applying OCR to the at least one DICOM SC image. For example, Tesseract OCR may be used on the whole image of each of the at least one DICOM SC image (or the converted TIFF images of the at least one DICOM SC image) to extract characters which have sharper contrast, large font size and thus easily extractable even though the overall accuracy might be low for other characters in the whole image. Certain keywords may be then needed to identify how the splitting could happen and what the grid geometry is like. This would be dependent on the content of the SC images, e.g., those respectively shown in FIGS. 1-5, and thus would be very use case based.

Generally, each SC image may have a specific format depending on its content and the scanner software producing it. For example, Syngo.Via writes its longitudinal strain measurements into grid sizes of 2×2, e.g., as shown in FIGS. 1, 4, and 5, and Ejection Fraction graphs in grid sizes of 2×3, e.g., as shown in FIG. 3. This information thus may facilitate clearly defining the keywords needed to identify the grid sizes as they may not vary much in different SC images of the same type. Further, there are a very limited number of types of SC image in each use-case setting and each type always follows the same format.

Figure 8A:
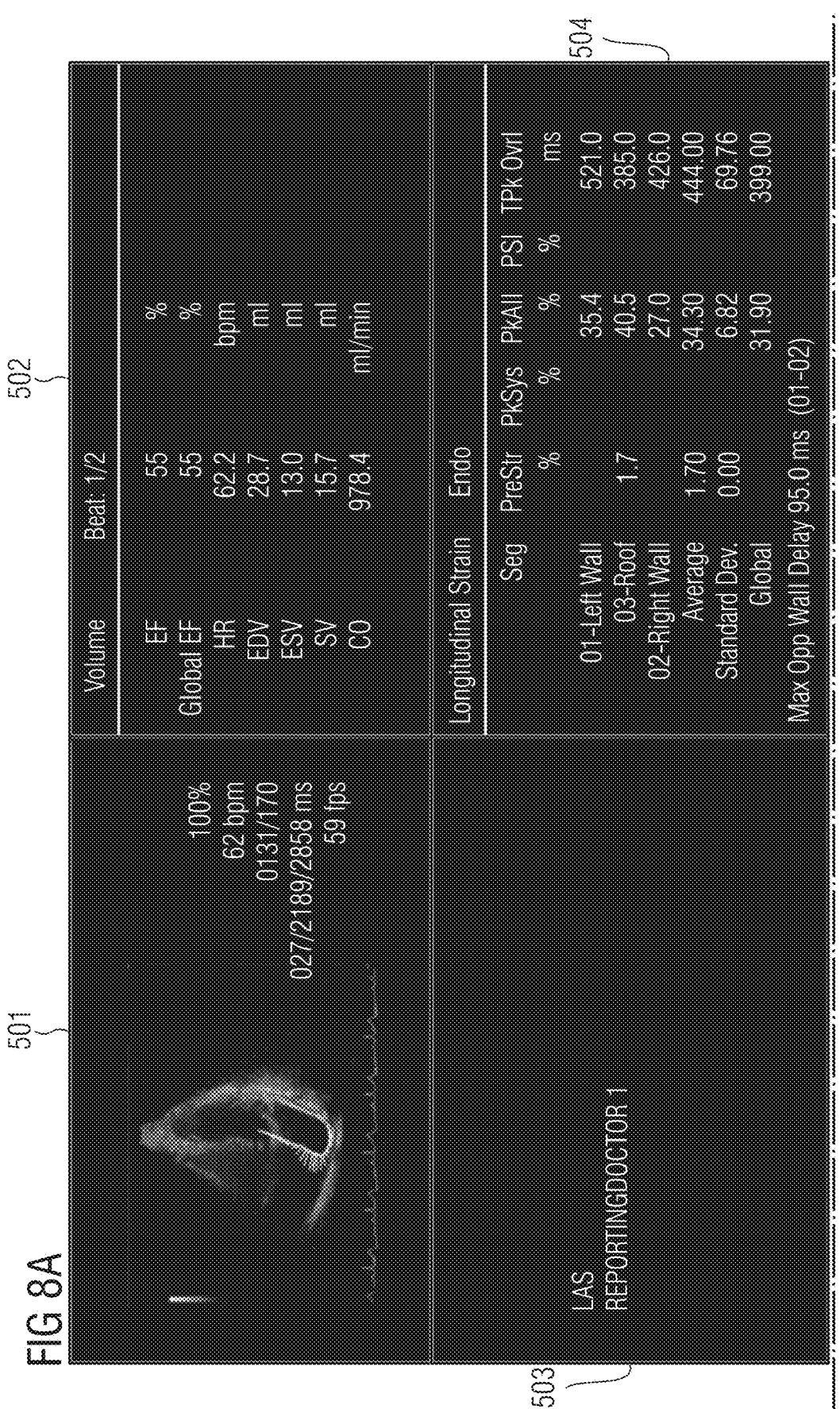
FIG. 8 (FIGS. 8A and 8B) schematically illustrates an exemplary workflow for splitting an SC image according to various examples.
Figure 8B:
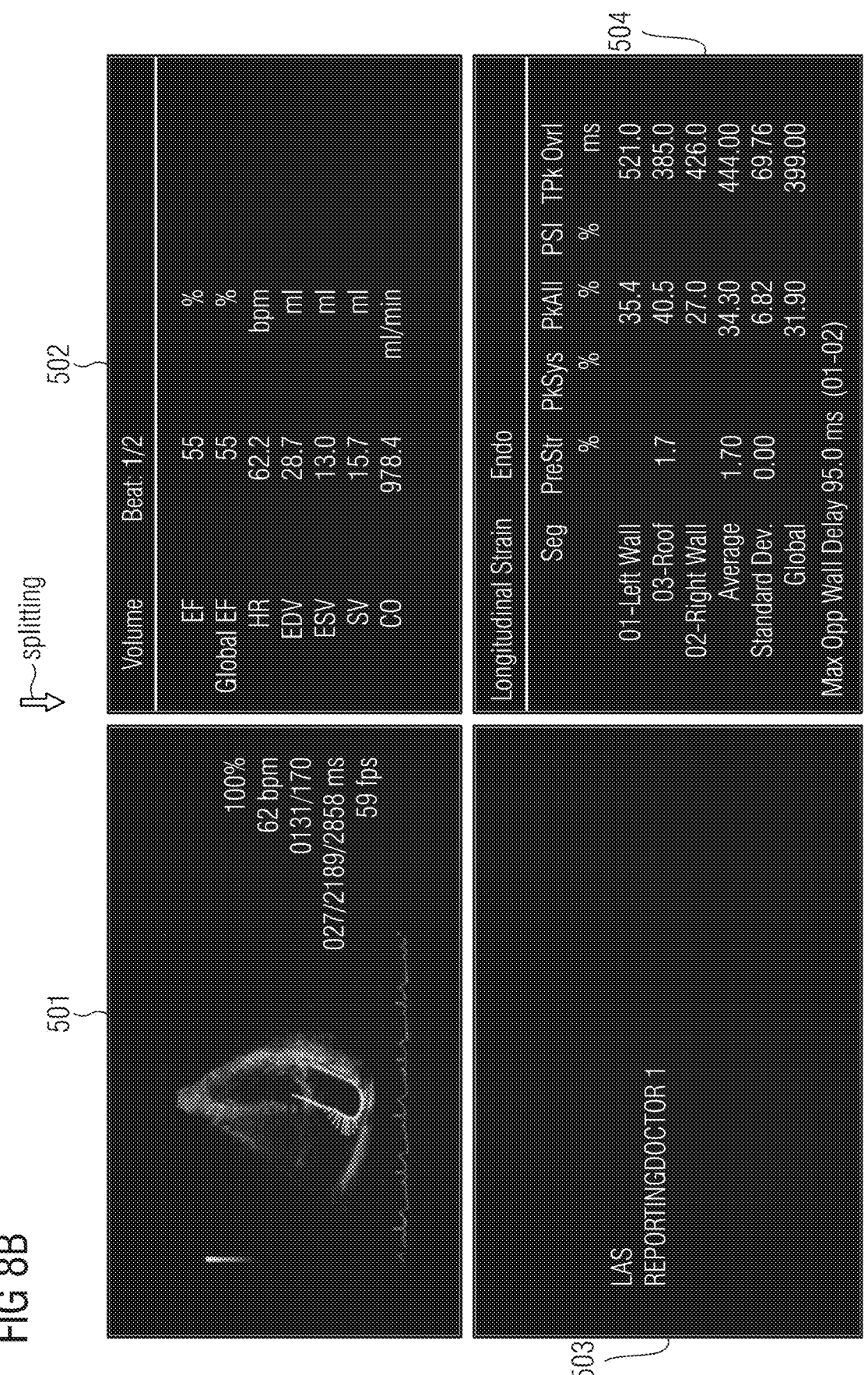
Figure 9A:
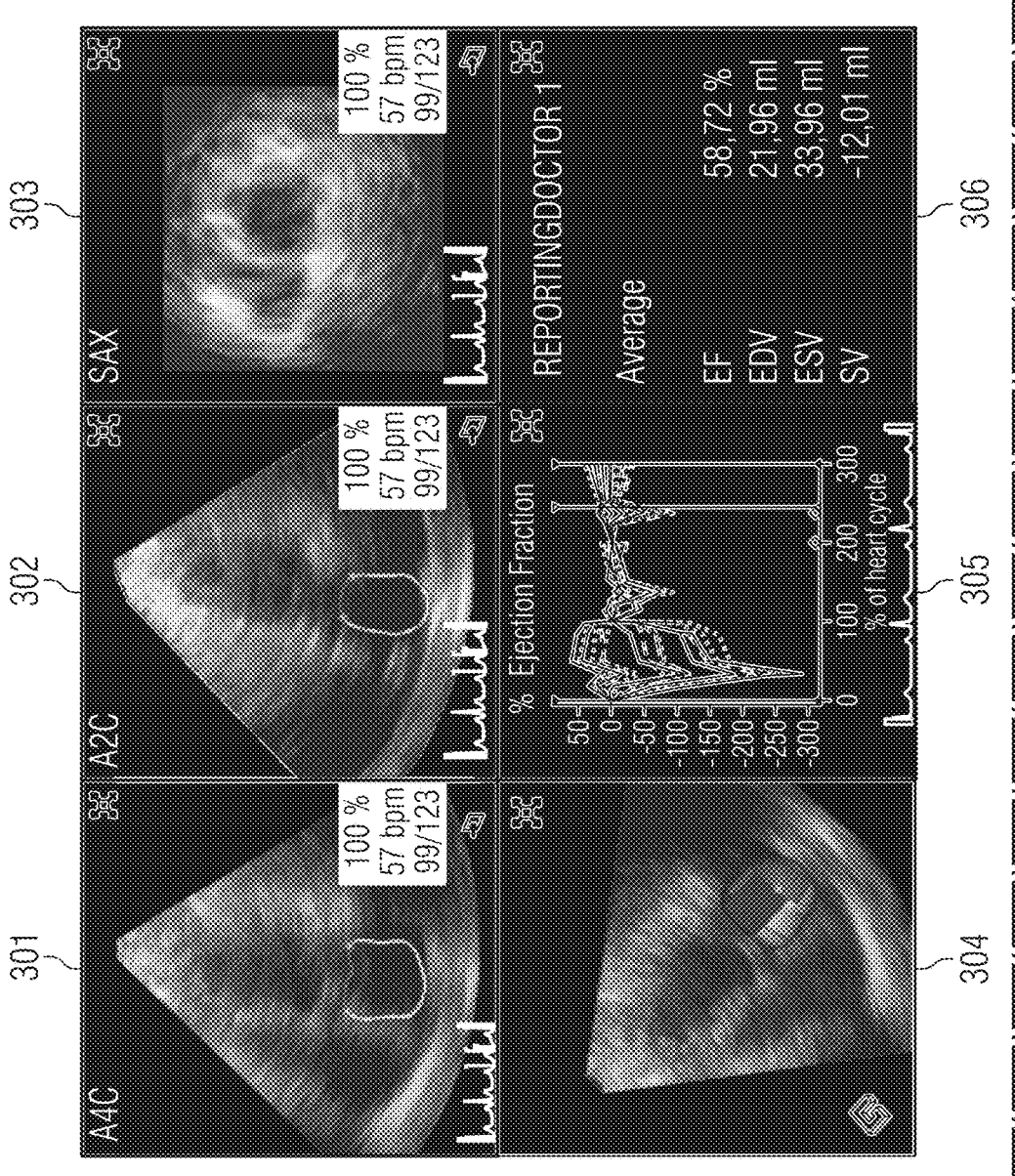
FIG. 9 (FIGS. 9A and 9B) schematically illustrates a further exemplary workflow for splitting a further SC image according to various examples.
Figure 9B:
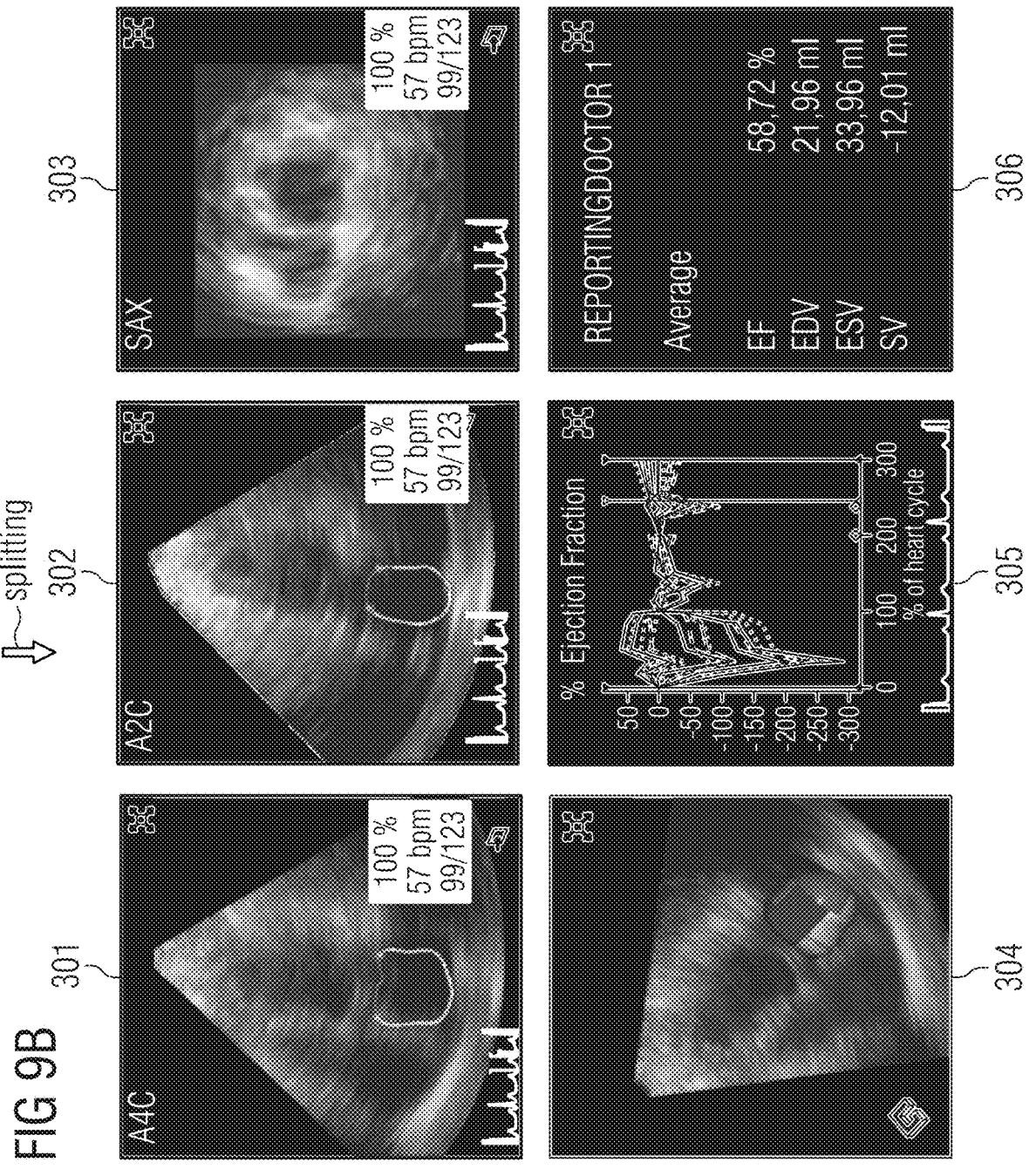

FIGS. 8 and 9 schematically illustrate exemplary workflows for splitting the SC image shown in FIGS. 5 and 3, respectively. Referring to FIG. 8, the splitting of the SC image of FIG. 5 can be based on a grid-size of 2*2 and/or keywords—Volume and Beat. Similarly, as shown in FIG. 9, the splitting of the SC image of FIG. 3 can be based on a grid-size of 2*3 and/or keywords—A4C and SAX. For example, as shown in FIG. 9, the whole SC image of FIG. 3 can be firstly split into two equal rows based on the grid-size of 2*3, and then each row can be split into three equal columns based on the keywords—A4C and SAX, i.e., the left and right columns are respectively starting from A4C and SAX, and the rest part is the middle column.

Alternatively, the configuration information may include a template of the at least one DICOM SC image, and the splitting of the at least one DICOM SC image is based on the template. For example, a template may be pre-defined and stored for each type of SC image, e.g., respective SC image shown in FIGS. 1-5. Then, the template can be selected from the pre-defined templates based on the type of the at least one DICOM SC image to be processed.

As shown in FIGS. 8 and 9, not every split sub-image contains the relevant characters to be extracted. For example, in FIG. 8, the required variables or relevant characters are only present in sections (or sub-images) 502 and 504. Similarly, in FIG. 9, such variables or characters are only contained in section (or sub-image) 306. Accordingly, the sub-images 502 and 504 are selected for the SC image shown in FIG. 8, and the sub-image 306 is selected for the SC image shown in FIG. 9.

To precisely select one or more sub-images containing the characters associated with the clinical data from the split sub-images, the selecting of the one or more sub-images may include respectively applying OCR to each of the split sub-images, e.g., 501-504 in FIG. 8, or 301-306 in FIG. 9; searching one or more pre-defined variables, e.g., EDV and/or ESV in FIGS. 8 and 9, respectively, associated with the clinical data in respective result of the OCR of respective sub-image, wherein the configuration information includes the one or more pre-defined variables; and selecting respective sub-images, e.g., 502 and 504 in FIG. 8 or 306 in FIG. 9, containing the one or more pre-defined variables, e.g., EDV and/or ESV, as the one or more sub-images containing the characters associated with the clinical data. As the respective OCR is applied on each of the split sub-images, the accuracy of the respective result of the OCR is more accurate than that of the OCR result of the whole SC image. Accordingly, the pre-defined variables can be identified more clearly and extracted more precisely.

Additionally, or optionally, different PSM modes could be applied to each sub-image and with manual sample verification, an optimal PSM value could be determined.

Optionally, after selecting the one or more sub-images containing the characters associated with the clinical data, margin alignment and trimming may be performed to centralize the content of the selected one or more sub-images.

Once the one or more sub-images containing the characters associated with the clinical data are selected, OCR is performed on the selected sub-images to extract the characters associated with the clinical data. The arrangement of the characters in each of the selected one or more sub-images may include row-wise, column-wise, or tabular. The method 2000 may optionally include determining an arrangement of the characters in each of the selected one or more sub-images. For example, referring to FIG. 8, the sub-images 502 and 504 are respectively row-wise and tabular. Different PSMs, e.g., PSM 4 and PSM 7, may be used to determine the arrangement of the characters in each of the selected one or more sub-images. For example, PSM 4 and PSM 7 may be respectively applied to each of the selected one or more sub-images to obtain a column-wise OCR result and a row-wise OCR result. Then, the arrangement of the characters can be determined by comparing the accuracy of the column-wise OCR result and the row-wise OCR result. Alternatively, the configuration information associated with the at least one DICOM SC image may include one or more PSMs, e.g., for each section.

When the arrangement of the characters is row-wise, the method 2000 may further include: splitting the selected one or more sub-images into rows, and applying OCR to each of the split rows to extract characters therein. Each character extracted from each of the split rows should be a whole character as else it means the row was split across text. Accordingly, the selected one or more sub-images would be split again until each character extracted from each of the split rows is a whole character.

FIG. 10 schematically illustrates an exemplary workflow for extracting row-wise characters from the selected sub-image 502. At 2040, the sub-image 502 may be split into rows. Then, at 2050, OCR may be applied to each of the split rows to extract characters therein. Further, at 2060, the characters associated with the pre-defined variables, e.g., EDV, ESV, and SV, included in the configuration information may be selected from the extracted characters of all the split rows. The units may be also extracted from the sub-image 502. Alternatively, the configuration information may include the units and the units may be added to the output based on the configuration information. Since the characters of the sub-image 502 is row-wise, PSM 7 may be used.

Similar to row-wise characters, when the arrangement of the characters is column-wise, the method 2000 may further include: splitting the selected one or more sub-images into columns and applying OCR to each of the split columns to extract characters therein.

When the arrangement of the characters is tabular, the method 2000 may further include: splitting the selected one or more sub-images into both rows and columns, respectively, applying OCR to each of the split rows and to each of the split columns to extract characters therein, respectively, and determining a position within a table of each of the extracted characters based on its positions in both the row-wisely and column-wisely extracted characters.

FIG. 11 schematically illustrates an exemplary workflow for extracting tabular characters from the selected sub-image 504. At 3010, the selected sub-image 504 is split into rows, and at 3020, the selected sub-image 504 is split into columns. At 3030, OCR is applied to each of the split rows to extract characters therein, and at 3040, OCR is applied to each of the split columns to extract characters therein. PSMs 4 and 7 may be utilized on each of the split columns and each of the split rows, respectively. At 3050, a position within a table of each of the extracted characters is determined based on its positions in both the row-wisely and column-wisely extracted characters. The pre-defined variables, e.g., column names—PreStr, PkSys, and PkAll, may be used to determine the width of corresponding columns. Similarly, the row names—Global and Average may be used to determine the height of corresponding rows. Alternatively, the common character(s) present in both the first row and the first column may be used to determine the width of the first column and the height of the first row, and from the second column onwards, the width is equally divided based on the remaining width of the whole sub-image, and from the second row onwards, the height is equally divided based on the remaining height of the whole sub-image.

The rich DICOM tag library could contain information in an SC image itself and there are well-defined tools to extract the DICOM tags. Hence, it is possible to identify if there are any DICOM header tags that could be used instead of extracting similar information from the pixel data of the SC image. For example, average dose applied while taking medical images could be stored in the CTDIvol (0018,9345) DICOM tag as well as embedded in the pixel data of the SC image. DICOM tags would contain information on the attributes of image acquisition and not of further diagnosis of the image. Moreover, the tags that are needed to add contextual information to the OCR-extracted clinical data can also be included in the configuration information. For example, PatientID, StudyID, AccessionNumber, and StudyDate are the DICOM tags that may be added to an output excel file in order to provide context.

Accordingly, the method 2000 may optionally include extracting DICOM tags from a header of the at least one DICOM SC image. The extracted DICOM tags may be paired with the extracted characters associated with the clinical data.

Figure 12:
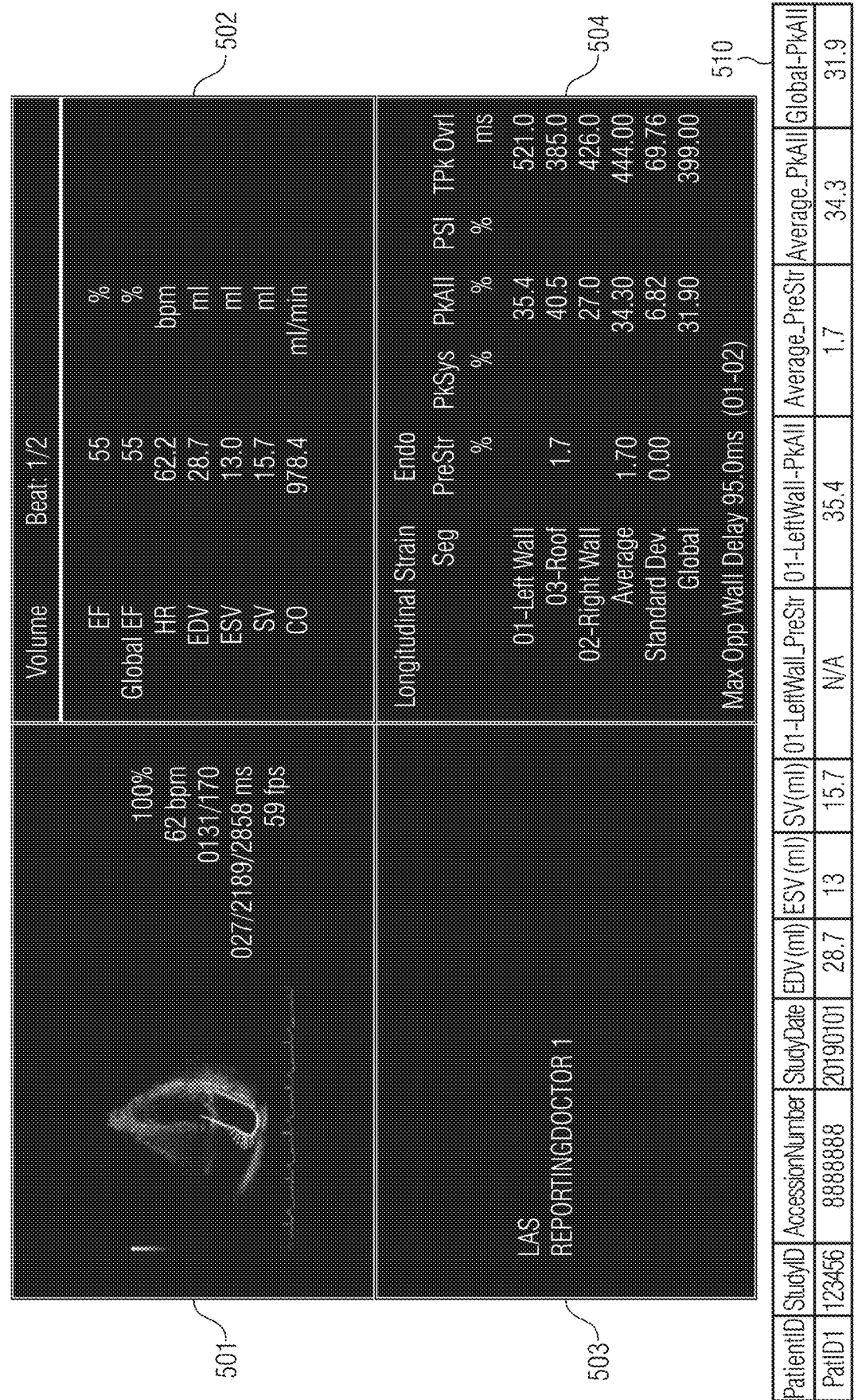
FIG. 12 schematically illustrates an exemplary output of extracted clinical data of an SC image.

FIG. 12 schematically illustrates an exemplary output 510 of extracted clinical data of an SC image. The output 510 is in Excel format and contains clinical data extracted from sub-images 502 and 504 as well as DICOM tags extracted from the header of the DICOM SC image, i.e., PatientID, StudyID, AccessionNumber and StudyDate, whose values are respectively PatID1, 123456, 8888888, and 20190101.

Alternatively, the method 2000 may optionally include removing patient health information, e.g., PatientID, StudyID, AccessionNumber and StudyDate, from the extracted characters associated with the clinical data. Thus, privacy of patients can be protected and thereby it is possible to share the extracted clinical data while complying with national data privacy laws.

In general, the above-outlined acts may be repeated for each SC image, and then the extracted clinical data, for example, is output in a new row of an Excel file like the output 510.

The method 2000 described above can be used to process any kind of DICOM SC image based on configuration information associated with the DICOM SC image to extract characters associated with clinical data. Thus, the method 2000 can extract whatever clinical data a user needs from any type of SC image. When processing different types of SC images, the configuration information can be customized based on a specific user's need, and/or be configured based on specific structures and content patterns of a specific type of SC image. Accordingly, there is no need to utilize different purpose-built techniques for different use cases. Further, the method 2000 also facilitates the utilization of clinical data extractable from SC images, e.g., in various research, while labor cost and/or time required for converting the characters associated with clinical data in SC images to text are significantly reduced due to the automatic nature of the method 2000, particularly for large datasets. The extracted clinical data can also facilitate the diagnosis of diseases, for example by automatically plugging such clinical data into radiology reports instead of radiologist dictations, and further can augment patient digital healthcare data and create a more accurate record for future analytics. In addition, the method 2000 can improve the accuracy of extraction of characters associated with clinical data from SC images, for example by splitting a whole SC image into sub-images and selecting sub-images containing characters to be extracted to condense pixel data of the DICOM SC image to only those regions that need OCR extraction. Further, specific techniques for respectively extracting row-wise, column-wise, and tabular characters can further improve the extraction accuracy.

DICOM is just an exemplary type of image that can be processed by the method 2000 but it is not a limitation of the method 2000. Other types of images or documents, such as a scanned document, a photo of a document, a scene-photo (for example the text on signs and billboards in a landscape photo), or subtitle text superimposed on an image (for example: from a television broadcast), can be processed by the method 2000 as well.

Figure 13:
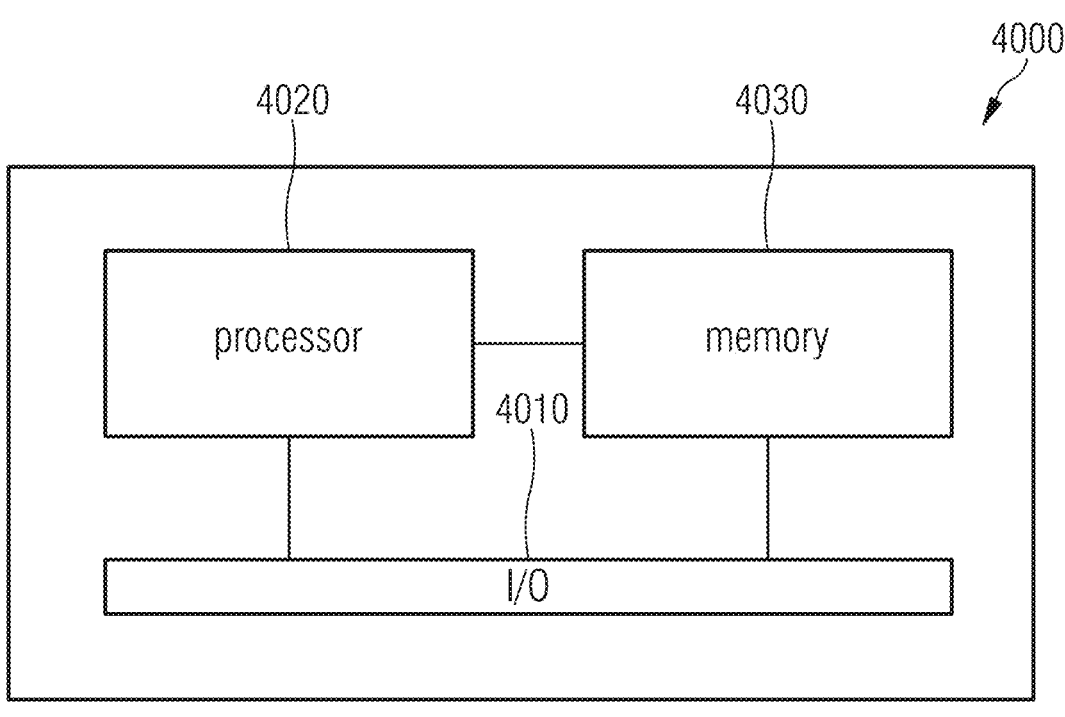
FIG. 13 is a block diagram of a computing device according to various examples.

FIG. 13 is a block diagram of a computing device (computer) 4000 according to various examples. The computing device 4000 provides a functionality of processing at least one DICOM SC image based on the method 2000.

The computing device 4000 may include at least one processor 4020, at least one memory 4030, and at least one input/output interface 4010. The at least one processor 4020 is configured to load program code from the at least one memory 4030 and execute the program code. Upon executing the program code, the at least one processor 4020 is configured to perform the method 2000.

According to the disclosure, a medical imaging scanner, such as a CT scanner, an MRI scanner, an ultrasound scanner, or an x-ray scanner, may include the computing device 4000 of FIG. 13. The medical imaging scanner may generate at least one DICOM SC image and process the generated SC image based on the method 2000.

Alternatively, the computing device 4000 may be embedded in or connected with the medical imaging scanner and thereby the medical imaging scanner may be also configured to perform the method 2000.

Alternatively, the computing device 4000 may be a personal computer (PC), another computer, or a workstation within a local network of a hospital or an institution or a node (server) of a cloud-based computing system or of an edge computing system.

To summarize, techniques have been described that facilitate the processing of any type of DICOM SC images to extract characters associated with whatever clinical data a user needs. The characters can be extracted from any type of DICOM SC image based on specific configuration information associated with the DICOM SC image. The more specific the configuration information, the more accurate the extraction of the characters. The extracted clinical data can further facilitate research, such as deep learning and/or data-mining research. The accuracy of the extraction of the characters can be further improved by splitting a whole SC image into sub-images and selecting sub-images containing characters to be extracted to condense pixel data of the DICOM SC image to only those regions that need OCR extraction. Further, specific techniques for respectively extracting row-wise, column-wise, and tabular characters can further improve the extraction accuracy.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

The invention claimed is:

1. A computer-implemented method comprising:

parsing, by at least one processor, at least one Digital Imaging and Communications in Medicine (DICOM) file comprising DICOM tags to identify at least one DICOM Secondary Capture (SC) image and to extract metadata associated with the at least one DICOM SC image;

determining, by the at least one processor, a SC image type based on at least one of a content pattern of pixel data of the at least one DICOM SC image or an image structure identified from the extracted metadata;

obtaining, by the at least one processor, configuration information associated with the determined SC image type, the configuration information comprising a grid-size defining sections within the pixel data of the at least one DICOM SC image, pre-defined variables associated with clinical data, and optical character recognition (OCR) page segmentation modes (PSMs) mapped to the sections;

segmenting, by the at least one processor, the pixel data of the at least one DICOM SC image into sub-images according to the grid-size;

selecting, by the at least one processor, one or more of the sub-images corresponding to the pre-defined variables associated with the clinical data and excluding remaining ones of the sub-images from further text extraction processing to condense the pixel data;

applying, by the at least one processor, optical character recognition to only the selected one or more sub-images using the OCR page segmentation modes;

generating, by the at least one processor, an output having a required structure of content comprising extracted textual content associated with the pre-defined variables; and storing the output.

2. The method of claim 1, further comprising:

converting, by the at least one processor, the at least one DICOM SC image to any one of the following image formats: tag image file format, raw image format, bitmap image file format, or portable network graphic format.

3. The method of claim 1, further comprising:

trimming, by the at least one processor, margins of the at least one DICOM SC image.

4. The method of claim 1, wherein the configuration information comprises one or more keywords of the characters associated with the clinical data, and the segmenting is further based on the one or more keywords.

5. The method of claim 4, wherein the one or more keywords are determined by the applying optical character recognition to the at least one DICOM SC image.

6. The method of claim 1, wherein the configuration information comprises a template of the at least one DICOM SC image, and the segmenting is further based on the template.

7. The method of claim 1, further comprising:

determining, by the at least one processor, an arrangement of the characters in each of the selected one or more sub-images, wherein the arrangement comprises row-wise, column-wise, or tabular.

8. The method of claim 7, wherein the arrangement is row-wise, the method further comprising:

splitting, by the at least one processor, the selected one or more sub-images into rows; and applying, by the at least one processor, the optical character recognition to each of the split rows to extract the characters therein.

9. The method of claim 7, wherein the arrangement is column-wise, the method further comprising:

splitting, by the at least one processor, the selected one or more sub-images into columns; and applying, by the at least one processor, the optical character recognition to each of the split columns to extract the characters therein.

10. The method of claim 7, wherein the arrangement is tabular, the method further comprising:

splitting, by the at least one processor, the selected one or more sub-images into both rows and columns, respectively;

applying, by the at least one processor, the optical character recognition to each of the split rows and to each of the split columns to extract the characters therein, respectively; and determining, by the at least one processor, a position within a table of each of the extracted characters based on positions in both the row-wisely and column-wisely extracted characters.

11. The method of claim 1, further comprising:

extracting, by the at least one processor, the DICOM tags from a header of the at least one DICOM SC image.

12. The method of claim 11, further comprising:

pairing, by the at least one processor, the extracted DICOM tags with the extracted characters associated with the clinical data; or removing, by the at least one processor, patient health information from the extracted characters associated with the clinical data.

13. A computing device comprising:

at least one processor; and at least one memory;

wherein upon loading and executing program code from the at least one memory, the at least one processor is configured to:

parse at least one Digital Imaging and Communications in Medicine (DICOM) file comprising DICOM tags to identify at least one DICOM Secondary Capture (SC) image and to extract metadata associated with the at least one DICOM SC image;

determine a SC image type based on at least one of a content pattern of pixel data of the at least one DICOM SC image or an image structure identified from the extracted metadata:

obtain configuration information associated with the determined SC image type, the configuration information comprising a predefined spatial extraction profile including sub-region coordinate boundaries within the pixel data of the at least one DICOM SC image, variable identifiers associated with clinical data, and optical character recognition (OCR) segmentation parameters mapped to the predefined sub-region coordinate boundaries;

segment the pixel data of the at least one DICOM SC image into sub-images according to the sub-region coordinate boundaries;

identify a subset of the plurality of sub-images corresponding to the variable identifiers associated with the clinical data and excluding remaining ones of the sub-images from further text extraction processing;

apply optical character recognition to only the identified subset of sub-images using the OCR segmentation parameters;

generate structured extracted clinical data comprising extracted textual content associated with the variable identifiers; and store the structured extracted clinical data in association with at least one DICOM metadata field.

14. The computing device of claim 13, wherein the at least one processor is further configured to trim margins of the at least one DICOM SC image.

15. The computing device of claim 13, wherein the at least one processor is further configured to determine an arrangement of the characters in each of the plurality of sub-images, wherein the arrangement comprises row-wise, column-wise, or tabular.

16. The computing device of claim 13, wherein the at least one processor is further configured to extract the DICOM tags from a header of the at least one DICOM SC image.

17. The computing device of claim 16, wherein the at least one processor is further configured to:

pair the extracted DICOM tags with the extracted characters associated with the clinical data; or remove patient health information from the extracted characters associated with the clinical data.

* * * * *